(12) United States Patent
Sato et al.

(10) Patent No.: US 8,748,561 B2
(45) Date of Patent: Jun. 10, 2014

(54) DEHYDROABIETIC ACID POLYMER, COMPACT, METHOD FOR PRODUCING DEHYDROABIETIC ACID POLYMER, AND DEHYDROABIETIC ACID COMPOUND

(75) Inventors: Kozo Sato, Kanagawa (JP); Toshimitsu Sakuma, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 13/576,161

(22) PCT Filed: Dec. 21, 2010

(86) PCT No.: PCT/JP2010/073032
§ 371 (c)(1),
(2), (4) Date: Jul. 31, 2012

(87) PCT Pub. No.: WO2011/096145
PCT Pub. Date: Aug. 11, 2011

(65) Prior Publication Data
US 2012/0322969 A1    Dec. 20, 2012

(30) Foreign Application Priority Data
Feb. 8, 2010 (JP) .................................. 2010-025989

(51) Int. Cl.
*C08G 63/02* (2006.01)
*G03G 9/00* (2006.01)

(52) U.S. Cl.
USPC ........................................ 528/298; 430/109.4

(58) Field of Classification Search
USPC ....................................................... 528/298
See application file for complete search history.

(56) References Cited

U.S. PATENT DOCUMENTS

| 2,472,437 A * | 6/1949 | Pratt | 562/404 |
| 6,107,447 A | 8/2000 | Kreuder et al. | |
| 2009/0069530 A1 | 3/2009 | Kimura et al. | |

FOREIGN PATENT DOCUMENTS

| JP | 59-022919 | 2/1984 |
| JP | 63-170328 | 7/1988 |
| JP | 4-153092 | 5/1992 |
| JP | 6-033395 | 2/1994 |
| JP | 6-087946 | 3/1994 |
| JP | 2000-500792 | 1/2000 |
| JP | 2007-292815 | 11/2007 |
| JP | 2008-274150 | 11/2008 |

OTHER PUBLICATIONS

Bilibin et al "Thermotropic polyesters" Macromol.Chem 186,1575-1591(1985).*
International Search Report PCT/JP2010/073032 dated Feb. 1, 2011.
Yolanda T. Pratt, Derivatives of Dehydroabietic Acid, Journal of the American Chemical Society, Aug. 1951, 73, 3803-7.

* cited by examiner

*Primary Examiner* — Ling Choi
*Assistant Examiner* — Gennadiy Mesh
(74) *Attorney, Agent, or Firm* — Young & Thompson

(57) ABSTRACT

Provided is a dehydroabietic acid polymer including a skeleton of the following formula (A) as a repeating unit:

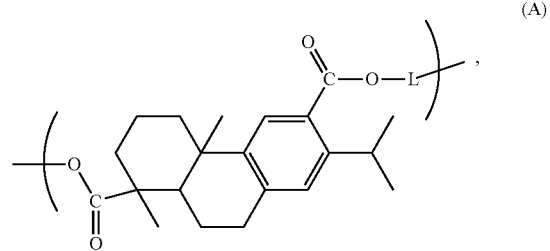

(A)

wherein L represents a divalent organic group. Methods for producing the dehydroabietic acid polymer are also provided. The dehydroabietic acid polymer has high resistance against moisture and water and high impact resistance. The dehydroabietic acid polymer can also be produced from a rosin-derived natural product.

9 Claims, No Drawings

DEHYDROABIETIC ACID POLYMER, COMPACT, METHOD FOR PRODUCING DEHYDROABIETIC ACID POLYMER, AND DEHYDROABIETIC ACID COMPOUND

TECHNICAL FIELD

The invention relates to a novel dehydroabietic acid polymer, a novel compact, a novel method for producing a dehydroabietic acid polymer, and a novel dehydroabietic acid compound.

BACKGROUND ART

In recent years, from the viewpoint of global environmental conservation, independence from petroleum-derived resources is being studied, and various natural resources are receiving attention. Independence from petroleum-derived resources is also being attempted in the plastic field, and polylactic acids produced from lactic acid obtained by glucose fermentation are widely used in packaging materials and the like.

According to Non-patent Document 1, polylactic acids have high transparency, but are inferior in impact resistance, heat resistance, and hydrolysis resistance. Therefore, the use of polylactic acids in compacts by injection molding and the like is limited.

In addition, not only polylactic acids, but, as described in Non-patent Documents 2 and 3, PET (polyethylene terephthalate) and PC (polycarbonate), which are petroleum-derived general-purpose polymers, have insufficient durability because they are readily hydrolyzed at a high temperature and humidity or in an acidic or alkaline environment, and improvement thereof is desired.

Rosin is a naturally-derived product collected from, for example, pine-tree gum. Rosin is composed of a mixture of various terpene carboxylic acids. Of these carboxylic acids, abietic acid is known to be useful as a polymer material (for example, see Patent Documents 1 and 2). For example, Patent Documents 1 and 2 disclose the use of a rosin-modified phenolic resin and a rosin-modified epoxy acid resin, which are prepared by modifying a phenolic resin or epoxy resin with abietic acid at the end of the resin, as binders for paints and the like. However, these resins are petroleum-dependent materials because they include a phenolic resin or an epoxy resin as the main skeleton, and thus do not reflect the viewpoint of global environmental conservation.

In addition, polymers prepared by polymerization of abietic acid with a polyalcohol are also known (for example, see Patent Document 3). However, since the polymers described in Patent Document 3 can be randomly polymerized to cause gelation, such polymers do not form linear polymers having a high molecular weight. Accordingly, these polymers are not suitable for industrial applications such as compacts.

PRIOR ART DOCUMENTS

Patent Documents

[Patent Document 1] Japanese Patent Application Laid-Open (JP-A) No. 2008-274150
[Patent Document 2] JP-A No. 6-87946
[Patent Document 3] JP-A No. 6-33395

Non-Patent Documents

[Non-patent Document 1] Hideto Tsuji "Polylactic Acid-Fundamentals and Applications of Plant-Derived Plastics", Yoneda Shuppan Co., 2008

[Non-patent Document 2] Eiichiro Takiyama "Polypolyester Resin Handbook", Nikkan Kogyo Shimbun, Ltd., 1988
[Non-patent Document 3] Seiichi Honma "Polycarbonate Resin Handbook", Nikkan Kogyo Shimbun, Ltd., 1992

DISCLOSURE OF THE INVENTION

Problems to be Solved by the Invention

The invention has been accomplished in view of the above-described problems, and is intended to achieve the following objectives.

More specifically, the invention is intended to provide a novel dehydroabietic acid polymer, a compact, a method for producing a dehydroabietic acid polymer, and a dehydroabietic acid compound, the dehydroabietic acid polymer being produced from a rosin-derived natural product and having high resistance against moisture and water and high impact resistance.

Means for Solving the Problems

The solution to the above-described problem is described below.

<1> A dehydroabietic acid polymer including a skeleton represented by following formula (A) as a repeating unit:

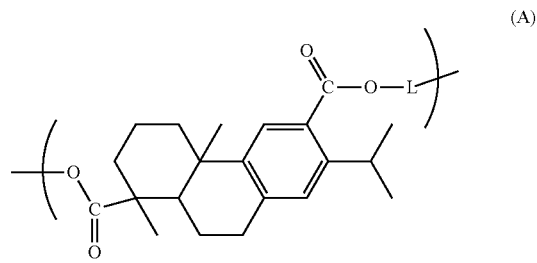

wherein, in formula (A), L represents a divalent organic group.

<2> The dehydroabietic acid polymer of <1>, wherein the organic group is an alkylene group, an arylene group, an aralkylene group or any combination thereof, wherein each of the alkylene group, the arylene group and the aralkylene group may contain an ether bond or an ester bond.

<3> The dehydroabietic acid polymer of <1> or <2>, wherein a weight average molecular weight of the polymer is from 5,000 to 500,000.

<4> The dehydroabietic acid polymer of any one of <1> to <3>, wherein the polymer is a homopolymer comprising the skeleton represented by formula (A).

<5> The dehydroabietic acid polymer of any one of <1> to <3>, wherein the polymer further includes another repeating unit.

<6> A composite material including the dehydroabietic acid polymer of any one of <1> to <5>.

<7> A compact made from the composite material of <6>.

<8> A method for producing a dehydroabietic acid polymer, the method including polycondensing 12-carboxydehydroabietic acid or its derivative with a diol compound.

<9> A dehydroabietic acid compound represented by following formula (D):

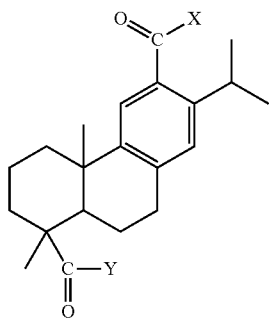

(D)

wherein, in formula (D), each of X and Y independently represents —OH, —OC$_n$H$_{2n+1}$, —OC$_n$H$_{2n}$OH, —OC$_6$H$_5$, or a halogen atom, and n represents an integer from 1 to 10; and at least one of X and Y represents —OC$_n$H$_{2n}$OH or —OC$_6$H$_5$, or both of X and Y represent a halogen atom.

<10> The dehydroabietic acid compound of <9>, wherein, in formula (D), each of X and Y independently represents —OC$_n$H$_{2n}$OH, n representing an integer from 1 to 10.

Effect of the Invention

According to the invention, a rosin-derived natural material is available for providing a dehydroabietic acid polymer, a compact, a method for producing a dehydroabietic acid polymer, and a dehydroabietic acid compound, the dehydroabietic acid polymer being provided as a novel polymer which has high resistance against moisture and water and high impact resistance.

BEST MODE FOR IMPLEMENTING THE INVENTION

[Dehydroabietic Acid Polymer]
A dehydroabietic acid polymer of the invention is further described below.
A dehydroabietic acid polymer of the invention is a polymer including a skeleton represented by following formula (A) as a repeating unit:

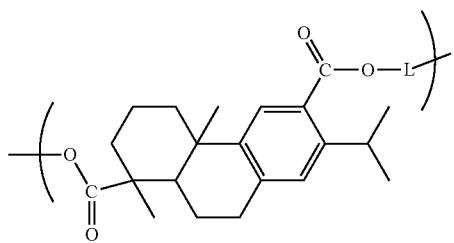

(A)

wherein, in formula (A), L represents a divalent organic group. L may be a divalent organic group containing plural different groups.

The divalent organic group represented by L is not particularly limited as long as it is a divalent group having a carbon atom in the basic skeleton of the structure. Preferred examples of the divalent organic group include an alkylene group, an arylene group, an aralkylene group, and combinations of these groups. These organic groups may contain one or more ether bonds or ester bonds, and may be substituted or unsubstituted.

Examples of the alkylene group include —C$_n$H$_{2n}$— (wherein n represents an integer from 1 to 18, preferably from 2 to 12) and —C$_m$H$_{2m}$—C$_6$H$_{10}$—C$_n$H$_{2n}$— (wherein m and n each independently represent an integer from 0 to 4, preferably 1 to 2; m and n cannot be 0 at the same time). More specific examples include —C$_2$H$_4$—, —C$_3$H$_6$—, —C$_4$H$_8$—, —C10H$_{20}$—, —CH$_2$CH(CH$_3$)—, —CH$_2$C$_6$H$_{10}$—CH$_2$—, and 1,4-trans-cyclohexylene group. These groups may be linear or branched.

Examples of the arylene group include a phenylene group, a biphenylene group, a naphthylene group, and —C$_6$H$_4$C(CH$_3$)$_n$C$_6$H$_4$— (n represents an integer from 1 to 4, preferably from 1 to 2). More specific examples include 1,4-phenylene group, 1,3-phenylene group, 4,4'-biphenylene group, 2,6-naphthylene group, and —C$_6$H$_4$C(CH$_3$)$_2$C$_6$H$_4$—. These groups may be linear or branched.

Examples of the aralkylene group include —C$_m$H$_{2m}$C$_6$H$_4$C$_n$H$_{2n}$— (wherein m and n each independently represent an integer from 0 to 4, preferably from 1 to 2; m and n cannot be 0 at the same time). More specific examples include —CH$_2$C$_6$H$_4$CH$_2$— and —CH$_2$CH$_2$C$_6$H$_4$CH$_2$CH$_2$—. These groups may be linear or branched.

Examples of the alkylene group, arylene group and aralkylene group containing an ether bond (—O—) or an ester bond (—COO— or —OCO—) include —C$_m$H$_{2m}$(OC$_n$H$_{2n}$)$_k$— (wherein k represents an integer from 1 to 8, preferably from 1 to 4, m and n each independently represent an integer from 1 to 4, preferably from 1 to 3), —C$_m$H$_{2m}$OC$_6$H$_4$OC$_n$H$_{2n}$— (wherein m and n each independently represent an integer from 1 to 10, preferably from 2 to 4), and —C$_m$H$_{2m}$OCOC$_6$H$_4$COOC$_n$H$_{2n}$— (wherein m and n each independently represent an integer from 1 to 10, preferably from 2 to 4). More specific examples include —CH$_2$CH$_2$OCH$_2$CH$_2$—, —CH$_2$CH$_2$(OCH$_2$CH$_2$)$_2$—, —CH$_2$CH$_2$(OCH$_2$CH$_2$)$_3$—, —CH$_2$CH$_2$OC$_6$H$_4$OCH$_2$CH$_2$—, —CH$_2$CH$_2$OCO—1,4-C$_6$H$_4$COOCH$_2$CH$_2$—, —CH$_2$CH$_2$OCO—1,3-C$_6$H$_4$COOCH$_2$CH$_2$—, —C$_3$H$_6$OCO-1,4-C$_6$H$_4$COOC$_3$H$_6$—, and —C$_4$H$_8$OCO-1,4-C$_6$H$_4$COOC$_4$H$_8$—. These groups may be linear or branched.

Preferred examples of the divalent organic group represented by L include —(CH$_2$)$_2$—, —(CH$_2$)$_3$—, —(CH$_2$)$_4$—, —(CH$_2$)$_8$—, —(CH$_2$)$_{10}$—, —CH$_2$CH$_2$OCH$_2$CH$_2$—, —CH$_2$CH(CH$_3$)—, —CH$_2$CH$_2$(OCH$_2$CH$_2$)$_2$—, —CH$_2$CH$_2$(OCH$_2$CH$_2$)$_3$—, —C$_6$H$_4$C(CH$_3$)$_2$C$_6$H$_4$—, —CH$_2$CH$_2$OC$_6$H$_4$OCH$_2$CH$_2$—, —CH$_2$CH$_2$OCO-1,4-C$_6$H$_4$COOCH$_2$CH$_2$—, —CH$_2$CH$_2$OCO-1,3-C$_6$H$_4$COOCH$_2$CH$_2$—, —C$_3$H$_6$OCO-1,4-C$_6$H$_4$COOC$_3$H$_6$—, —C$_4$H$_8$OCO-1,4-C$_6$H$_4$COOC$_4$H$_8$—, —CH$_2$C$_6$H$_{10}$(1,4-cyclohexylene)CH$_2$—, —C$_6$H$_4$—, —C$_6$H$_4$C$_6$H$_4$—, —C$_6$H$_4$C(CH$_3$)$_2$C$_6$H$_4$—, and combinations of these groups.

Particularly preferably, L represents —(CH$_2$)$_3$—, —(CH$_2$)$_4$—, —(CH$_2$)$_{10}$—, —CH$_2$CH$_2$OCH$_2$CH$_2$—, —CH$_2$CH$_2$(OCH$_2$CH$_2$)$_2$—, —C$_6$H$_4$C(CH$_3$)$_2$C$_6$H$_4$—, —CH$_2$CH$_2$OC$_6$H$_4$OCH$_2$CH$_2$—, —CH$_2$CH$_2$OCO-1,4-C$_6$H$_4$COOCH$_2$CH$_2$—, —CH$_2$CH$_2$OCO-1,3-C$_6$H$_4$COOCH$_2$CH$_2$—, —C$_3$H$_6$OCO-1,4-C$_6$H$_4$COOC$_3$H$_6$—, —C$_4$H$_8$OCO-1,4-C$_6$H$_4$COOC$_4$H$_8$—, or combinations of these groups.

The polymer of the invention includes formula (A) as a repeating unit, and may be a homopolymer of formula (A), or a copolymer of formula (A) with another monomer.

The another monomer is not particularly limited, and may be selected from known or commercially available ones. Preferred examples include the followings, which may be used alone or two or more of them:

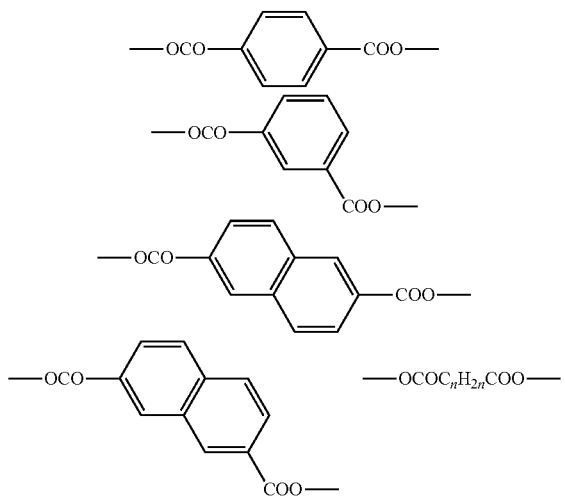

(wherein n represents an integer from 1 to 20, preferably from 2 to 10)

In a case in which the dehydroabietic acid polymer of the invention is a copolymer including another monomer, the molar ratio between the repeating unit represented by formula (A) and another monomer is not particularly limited, and may be appropriately determined according to the intended function and use. For example, the ratio is about 1:0.2 to 1:3, preferably about 1:0.5 to 1:2.

The weight average molecular weight of a dehydroabietic acid polymer of the invention is not particularly limited, preferably about 5,000 to 500,000, more preferably about 10,000 to 300,000. In a case in which the weight average molecular weight is within this range, a dehydroabietic acid polymer is further superior in mechanical strength and formability such as film forming ability, and is advantageous for industrial use. The weight average molecular weight in the invention is determined based on molecular weight measurement (based on polystyrene) by gel permeation chromatography (GPC).

A dehydroabietic acid polymer of the invention includes the polymers of chemically transformed dehydroabietic acid derivatives prepared by introducing a further substituent to the dehydroabietic acid polymer having a repeating unit containing a dehydroabietic acid skeleton. Examples of the substituent include halogen atoms (for example, F, Cl, and Br), alkyl groups (for example, a methyl group and an isopropyl group), and alkoxy groups (for example, a methoxy group and an ethoxy group). In formula (A) of the invention, the steric configuration of the asymmetric carbon at the 10- and 18-positions may be R or S configuration. In normal cases, the 10-position is S configuration, and the 18-position is R configuration.

A dehydroabietic acid polymer of the invention includes the above-described skeleton, more specifically, a polyester skeleton obtained by polymerization of a 12-carboxy dehydroabietic acid derivative with a diol compound as a main skeleton. Therefore, it has high resistance against moisture and water, high impact resistance, and good formability such as film forming ability. The reason for this is likely that a linear polymer with a relatively high molecular weight is readily formed because the dehydroabietic acid skeleton, which is chemically stable and hydrophobic, is linked by ester bonds at the 12- and 18-positions.

The dehydroabietic acid polymer of the invention may be obtained from pine-tree gum-derived rosin which is available as a biomass resource, and exhibits high impact resistance and high resistance against moisture and water. In addition, it has good formability such as film forming ability. Accordingly, the dehydroabietic acid polymer of the invention is useful as a novel biomass polymer which is superior to conventional biomass polymers such as polylactic acid in impact resistance and resistance against moisture and water. The polymer of the invention is suitable for the applications where high impact resistance high resistance against moisture and water, or the like is required. The polymer is useful for various applications in various forms such as a sheet, a film, fibers, a molding material, a toner binder for a copier (for example, a xerographic copier), a resin for printing ink, or an adhesive.

[Method for Producing Dehydroabietic Acid Polymer]

A method of the invention for producing a dehydroabietic acid polymer is further described below.

A dehydroabietic acid polymer of the invention may be obtained though, for example, polymerization of 12-carboxydehydroabietic acid or its derivative with a diol compound. As necessary, another monomer (for example, dicarboxylic acid) is further polymerized with the polymer to obtain a dehydroabietic acid copolymer.

12-Carboxydehydroabietic acid is represented by following formula (B).

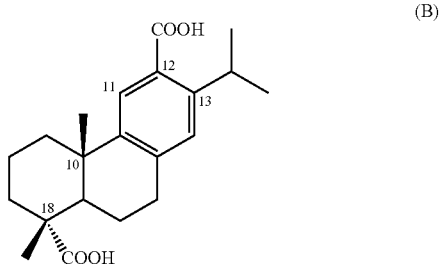 [SMILES: CC(C)c1cc2c(cc1C(=O)O)[C@@]1(C)CCC[C@@](C)(C(=O)O)C1CC2]

12-Carboxydehydroabietic acid or its derivative is represented, for example, by following formula (C):

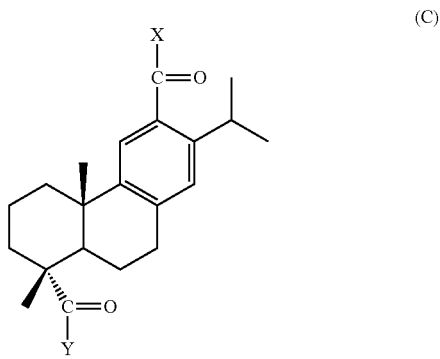

wherein, in formula (C), each of X and Y independently represents —OH, —OR, —OCOR, —OCOOR, —OSO$_2$R, NR$_2$, a halogen atom (for example, F, Cl, or Br), an imidazolyl group, or a triazolyl group; R represents an alkyl group (preferably having 1 to 4, more preferably 1 or 2 carbon atoms), an aralkyl group (preferably having 7 to 10, more preferably 7 to 9 carbon atoms), an aryl group (preferably having 6 to 12, more preferably 6 to 9 carbon atoms), or the like. Among these groups, X is preferably —OH, —OR, or the like, and more preferably —OH. Y is preferably —OH or —OR.

Examples of the diol compound include aliphatic diols such as ethylene glycol, 1,2-propanediol, 1,3-propanediol, 1,4-butanediol, 1,6-hexanediol, 1,8-octanediol, 1,10-decanediol, 1,12-dodecanediol, diethylene glycol, triethylene glycol, tetraethylene glycol, and 1,4-bis(2-hydroxyethoxy) benzene; and aromatic diols such as hydroquinone, 4,4'-biphenol, and 2,2-bis(4-hydroxyphenyl)propane. From the viewpoint of plant content, for example, 1,3-propanediol or 1,10-decanediol is more preferred. In addition, the compound having a hydroxyl group and/or a carboxyl group in addition to the two hydroxyl groups is also useful for modifying the higher-order structure of the polymer to be formed. Examples of the compound include citric acid, malic acid, tartaric acid, glyceric acid, glycerol, trimethylolpropane, and pentaerythritol. These diol compounds may be used alone or in combination of two or more thereof.

12-Carboxydehydroabietic acid used for the production of the dehydroabietic acid polymer of the invention may be prepared from, for example, rosin.

Rosin is a resin component collected from pine-tree gum, and typically classified into three types; "gum rosin", "tall rosin", and "wood rosin", according to the method of collection. The components of rosin vary depending on the method of collection and the growing land of the pine. In general, rosin is a mixture of diterpene resin acids such as abietic acid (1), neoabietic acid (2), parastrinic acid (3), levopimaric acid (4), dehydroabietic acid (5), pimaric acid (6), and isopimaric acid (7), the structures of which are shown below.

(1)
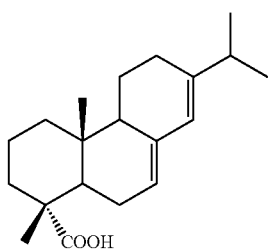

(2)
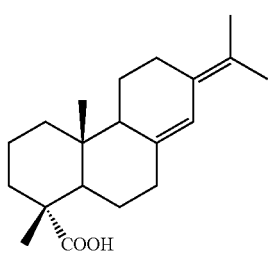

(3)
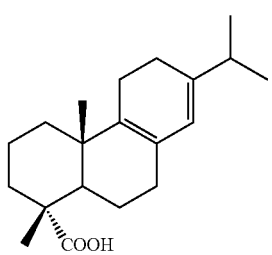

(4)
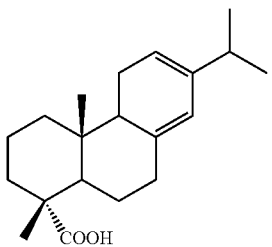

(5)
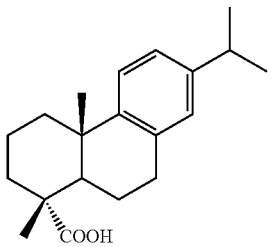

(6)
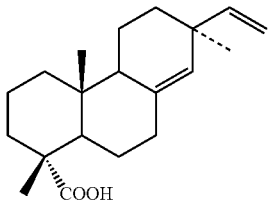

(7)
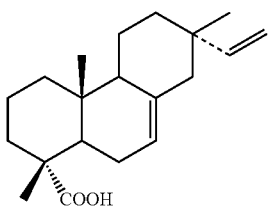

Among these diterpene resin acids, each of the compounds represented by (1) to (4) cause dismutation by, for example, heat treatment in the presence of a catalyst such as an apatite catalyst, and are denatured into dehydroabietic acid (5) and dihydroabietic acid (8) having the following structure. This process is carried out with reference to, for example, JP-A No. 2002-284732.

(8)

More specifically, 12-carboxydehydroabietic acid necessary for synthesizing the dehydroabietic acid polymer of the invention can be industrially produced at a low cost from dehydroabietic acid (5), which is readily obtained by subjecting rosin composed of various resin acids to appropriate chemical treatment.

In addition, 12-position of dehydroabietic acid has a high electron density, and susceptible to various aromatic electrophilic substitution. More specifically, acylation or halogenation can readily occur, so that a carboxyl group is introduced to the 12-position by functional group transformation through a known reaction. The method for producing a dehydroabietic acid polymer of the invention is demonstrated more specifically by the following synthetic pathway.

(Synthetic Pathway)

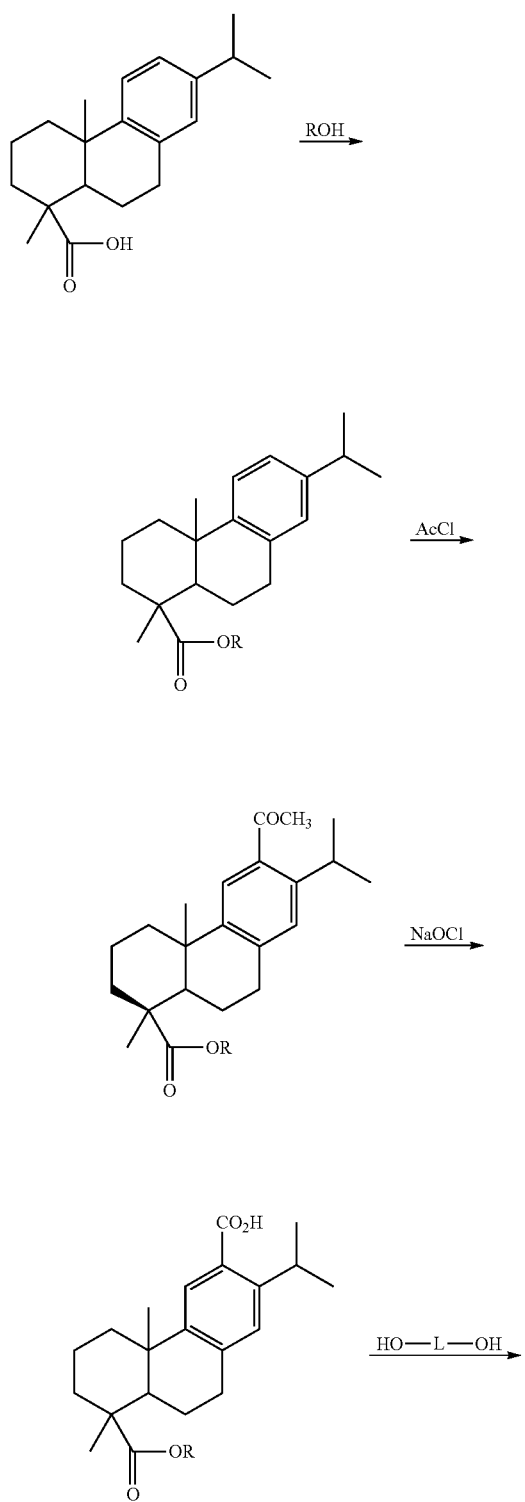

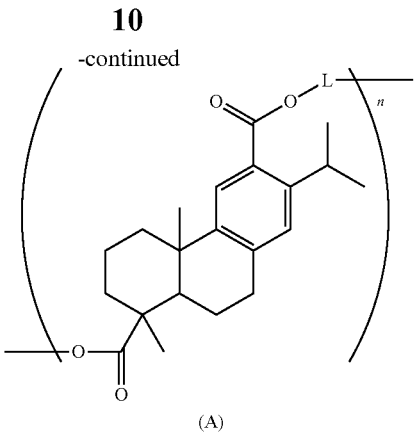

(A)

The process of synthesizing the polyester polymer obtained by polycondensation of 12-carboxydehydroabietic acid (or its derivative) with a diol compound shown by the above-described synthetic pathway is further described below.

In the synthetic pathway, the step of synthesizing the polymer (polyester polymer) having a repeating unit represented by formula (A) is achieved by polycondensation of a compound represented by formula (C) with a diol compound by a known method.

Specific examples of the synthetic method include a method described in New Polymer Experiment 3, Polymer Synthesis and Reaction (2), p. 78 to 95, Kyoritsu Shuppan Co., Ltd. (1996) (for example, interesterification method, direct esterification method, polycondensation method using an acid chloride, low temperature solution polymerization method, high temperature solution polycondensation method, and interfacial polycondensation method). In the invention, an interesterification and a direct esterification method are particularly preferred.

An interesterification method is a method includes heating a diol compound and a dicarboxylate in a molten or solution state, as necessary in the presence of an acid catalyst, thereby causing dealcoholization polycondensation to form a polyester.

A direct esterification method is a method includes heating and dehydrating a diol compound and a dicarboxylic acid compound in a molten or solution state in the presence of an acid catalyst, thereby causing polycondensation to form a polyester.

An acid chloride method includes heating a diol compound and a dicarboxylic acid chloride compound in a molten or solution state, as necessary in the presence of a base catalyst, thereby causing dehydrochlorination, and a polyester being formed by polycondensation.

An interfacial polymerization method includes dissolving the diol compound in water, and the dicarboxylic acid chloride compound in an organic solvent, and causing polycondensation at the water/organic solvent interface in the presence of an alkali presence using a phase transfer catalyst, thereby forming a polyester.

The synthesis examples of the polymer composed of a repeating unit represented by Formula (A) are further described in the below-described examples.

According to the invention, in the synthesis of a polyester polymer by the above-described synthetic pathway, 12-carboxydehydroabietic acid (or its derivative) may be combined with another dicarboxylic acid to synthesize a polyester copolymer. The synthesis example of the copolymer may be carried out with reference to a known method. In general, 12-carboxydehydroabietic acid is heated at a high temperature (preferably about 200° C. to 280° C.) together with an appropriate amount of another dicarboxylic acid and a diol compound under reduced pressure, and low boiling point compounds such as water and an alcohol formed as a result of the reaction are evaporated and polycondensed, thereby obtaining a copolymer.

Examples of the another dicarboxylic acid useful for the synthesis of the above-described copolymer include various aliphatic and aromatic dicarboxylic acids. Preferred examples thereof include succinic acid, adipic acid, sebacic acid, 1,4-cyclohexane dicarboxylic acid, maleic acid, fumaric acid, terephthalic acid, isophthalic acid, 2,6-naphthalenedicarboxylic acid, and 1,5-naphthalenedicarboxylic acid.

[Dehydroabietic Acid Compound]

A dehydroabietic acid compound (intermediate compound) of the invention is represented by following formula (D). The following compound is suitable for the production of a dehydroabietic acid polymer of the invention:

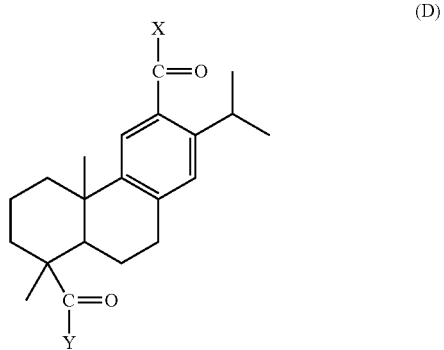

(D)

wherein, in formula (D), each of X and Y independently represents —OH, —$OC_nH_{2n+1}$, —$OC_nH_{2n}OH$, —$OC_6H_5$, or a halogen atom (for example, F, Cl, or Br). The halogen atom is preferably Cl; n represents an integer from 1 to 10, preferably from 1 to 4; in the invention, it is preferred that at least one of X and Y is —$OC_nH_{2n}OH$ or —$OC_6H_5$, or both of X and Y are halogen atoms; it is even more preferred that each of X and Y independently represents —$OC_nH_{2n}OH$; n represents an integer from 2 to 10, preferably from 2 to 4; —$OC_nH_{2n+1}$ and —$OC_nH_{2n}OH$ may be linear or branched. In Formula (D) of the invention, the steric configuration of the asymmetric carbon at the 10- and 18-positions may be R or S configuration. In general, the 10-position is S configuration, and the 18-position is R configuration.

[Composite Material Containing Dehydroabietic Acid Polymer]

A dehydroabietic acid polymer of the invention may be used alone as a polymer material. Alternatively, a dehydroabietic acid polymer of the invention may be blended with various materials to make composite materials. The composite materials containing a dehydroabietic acid polymer of the invention are further described below.

In order to improve the physical properties, a dehydroabietic acid polymer of the invention may be blended with various materials to make composite materials. In a case in which a dehydroabietic acid polymer is made into a composite material, a dehydroabietic acid polymer is preferably blended with a different polymer to make a polymer alloy and/or with a filler, thereby improving impact resistance, heat resistance, durability, formability, and the like.

The polymers used to make a polymer alloy may be a combination of plural dehydroabietic acid polymers of the invention having different polymer properties, or a combination of dehydroabietic acid polymer of the invention and another polymer.

A polymer used to make a polymer alloy, other than a dehydroabietic acid polymer of the invention, is not particularly limited, and may be selected from known or commercially available ones. Examples of the polymer include:

1) olefin resins (for example, homopolymers of ethylene or an α-olefin such as propylene, 1-butene, 1-pentene, 1-hexene, or 4-methyl-1-pentene, or cycloolefin such as cyclopentene, cyclohexene, cyclooctene, cyclopentadiene, 1,3-cyclohexadiene, bicyclo[2.2.1]hepta-2-ene, tricyclo[4.3.0.1$^{2,5}$]deca-3,7-diene, or tetracyclo[4.4.0.1$^{2,5}$.1$^{7,10}$]dodeca-3-ene; copolymers of the above-described α-olefins; and copolymers of α-olefins with another copolymerizable monomer such as vinyl acetate, maleic acid, vinyl alcohol, methacrylic acid, methyl methacrylate, and ethyl methacrylate);

2) polyester resins (for example, copolymers of a dicarboxylic acid monomer such as terephthalic acid, isophthalic acid, 2,6-naphthalenedicarboxylic acid, 1,4-naphthalenedicarboxylic acid, succinic acid, adipic acid, or sebacic acid with a diol or polyalcohol monomer such as ethylene glycol, propylene glycol, 1,4-butylene glycol, 1,4-cyclohexane dimethanol, diethylene glycol, triethylene glycol, polypropylene glycol, polyoxytetramethylene glycol, an alkylene oxide adduct of a bisphenol compound or its derivative, trimethylolpropane, glycerol, or pentaerythritol; and polycondensates of hydroxycarboxylic acids such as lactic acid, β-hydroxy butyric acid, p-hydroxybenzoic acid, or 2,6-hydroxynaphthoic acid);

3) polyamide resins (polymers containing an acid amide bond in the chain thereof obtained by polycondensation of, for example, a lactam with three or more members, a polymerizable ω-amino acid, or a dibasic acid with a diamine, specific examples including polymers of ε-caprolactam, aminocaproic acid, enantholactam, 7-aminoheptanoic acid, 11-aminoundecanoic acid, 9-aminononanoic acid, α-pyrrolidone, α-piperidone, or the like, polymers and copolymers thereof obtained by polycondensation of a diamine such as hexamethylenediamine, nonamethylenediamine, undecamethylenediamine, dodecamethylenediamine, or metaxylylenediamine with a dicarboxylic acid such as terephthalic acid, isophthalic acid, adipic acid, sebacic acid, dodecane dibasic acid, or glutaric acid, such as nylon-4, nylon-6, nylon-7, nylon-8, nylon-11, nylon-12, nylon-6,6, nylon-6,10, nylon-6,11, nylon-6,12, nylon-6T, nylon-6/nylon-6,6 copolymer, nylon-6/nylon-12 copolymer, nylon-6/nylon-6T copolymer, and nylon-6I/nylon-6T copolymer);

4) rubbers and elastomers (for example, natural rubber, isoprene rubber, butadiene rubber, 1,2-polybutadiene rubber, styrene-butadiene rubber, chloroprene rubber, nitrile rubber, butyl rubber, ethylene-propylene rubber, chlorosulfonated polyethylene, acrylic rubber, epichlorohydrin rubber, polysulfide rubber, silicone rubber, fluorocarbon rubber, and urethane rubber); and 5) other resins such as polycarbonate resins, acrylic resins, urethane resins, polyvinyl alcohols, vinyl chloride resins, styrene resins, polyacrylonitriles, poly(vinylidene chloride), fluorocarbon resins, polyacetals, polysulfones, ABS, and polyether ether ketones.

Among the above-described polymers used for making polymer alloys, from the viewpoint of plant content, polylactic acid, poly-β-hydroxybutyric acid, and polybutylene succinate, for example, are preferred.

A polymer alloy may be prepared in accordance with a known method. In general, a melt kneading process is used, but if simple kneading causes phase separation, a homogeneous phase may be formed by using a compatibilizer, causing secondary block polymerization or graft polymerization, or dispersing one polymer in clusters.

In order to make a polymer alloy without impairing the properties of the dehydroabietic acid polymer of the invention, the content (mass base) of the dehydroabietic acid polymer of the invention in the polymer alloy is generally from 1 to 100%, preferably from 20 to 100%, and more preferably from 50 to 100%.

A dehydroabietic acid polymer of the invention may be blended with various fillers to achieve desired polymer properties. The addition of a filler is particularly effective for improvement of heat resistance, durability, and impact resistance.

The filler may be inorganic or organic.

Preferred examples of the inorganic filler include fibrous inorganic fillers such as glass fiber, carbon fiber, graphite fiber, metal fiber, potassium titanate whisker, aluminum borate whisker, magnesium whisker, silicon whisker, wollastonite, sepiolite, slag fiber, xonotlite, ellestadite, gyps fiber, silica fiber, silica-alumina fiber, zirconia fiber, boron nitride fiber, silicon nitride fiber, and boron fiber; and plate-shaped or granular inorganic fillers such as glass flake, non-swelling mica, fullerene, carbon nanotube, carbon black, graphite, metal foil, ceramic bead, talc, clay, mica, sericite, zeolite, bentonite, dolomite, kaolin, fine powder silicic acid, feldspar powder, potassium titanate, Shirasu balloon, calcium carbonate, magnesium carbonate, barium sulfate, calcium oxide, aluminium oxide, titanium oxide, magnesium oxide, aluminium silicate, silicon oxide, aluminum hydroxide, magnesium hydroxide, gyps, novaculite, dawsonite, and clay.

Preferred examples of the organic filler include fibrous organic fillers obtained from synthetic fibers such as cellulose (nano)fiber, polyester fiber, nylon fiber, acrylic, fiber, regenerated cellulose fiber, acetate fiber, and aramid fiber, natural fibers such as kenaf, ramie, cotton, jute, hemp, sisal, Manila hemp, flax, linen, silk, wool, as well as microcrystalline cellulose, sugarcane, wood pulp, paper scrap, and waste paper; and granular organic fillers such as an organic pigment.

A composite material including a dehydroabietic acid polymer of the invention may contain a flame retardant and the like. The flame retardant is not particularly limited as long as it reduces flammability of polymer materials or retards the spread of fire, and may be selected from known or commercially available ones. Examples of the flame retardant include halogen (bromine and chlorine) compounds, phosphorus compounds (for example, aromatic phosphates and polyphosphates), silicon-containing flame retardants, nitrogen compound-based flame retardants, and inorganic flame retardants. In particular, from the viewpoint of environmental safety, aluminum hydroxide, magnesium hydroxide and the like are preferred. The content of the flame retardant is normally 30 parts by mass or less, preferably 10 parts by mass or less with reference to 100 parts by mass of the polymer of the invention.

Other material (flame retardant aid) used in combination with the flame retardant to enhance flame retardancy, and to form a carbide film on the resin surface thereby retarding the spread of fire is also useful as a component of the composite material including a dehydroabietic acid polymer of the invention. Specific preferred examples of the flame retardant aid include inorganic ones such as antimony compounds, and organic aromatic compounds (for example, phenol derivatives).

A dehydroabietic acid polymer of the invention may contain a plasticizer, thereby further improving flame retardancy and formability. The plasticizer may be selected from those commonly used for polymer molding. Examples of the plasticizer include polyester plasticizers, glycerol plasticizers, polyvalent carboxylate plasticizers, polyalkylene glycol plasticizers, and epoxy plasticizers. The content of the plasticizer is normally 30 parts by mass or less, preferably 10 parts by mass or less with reference to 100 parts by mass of the polymer of the invention.

A dehydroabietic acid polymer of the invention may further contain common additives other than the above-described ones, such as a stabilizer, an impact resistance improver, a crystal nucleating agent, a lubricant, an antistatic agent, a surfactant, a pigment, a dye, a filler, an antioxidant, a processing aid, an ultraviolet absorber, an anti-fogging agent, an antibacterial agent, or a mildewproofing agent, which may be used alone or in combination of two or more of them.

A composite material of the invention obtained by blending the above-described materials may be formed (molded) by various methods. Examples of the molding method include extrusion molding and injection molding. The application of the compact thus obtained is not particularly limited, and examples of the application include components of automobiles, home appliances, electric/electronic devices (for example, OA/media equipment, optical equipment, and communication equipment), machine parts, house building materials, containers, and various bottles such as cosmetic and beverage bottles.

EXAMPLES

The invention is further described below with reference to examples, but the invention will not be limited to these examples.

Firstly, 12-carboxydehydroabietic acid derivative used for the synthesis of a dehydroabietic acid polymer of the invention was synthesized as the following synthetic pathway.

(Synthetic Pathway)

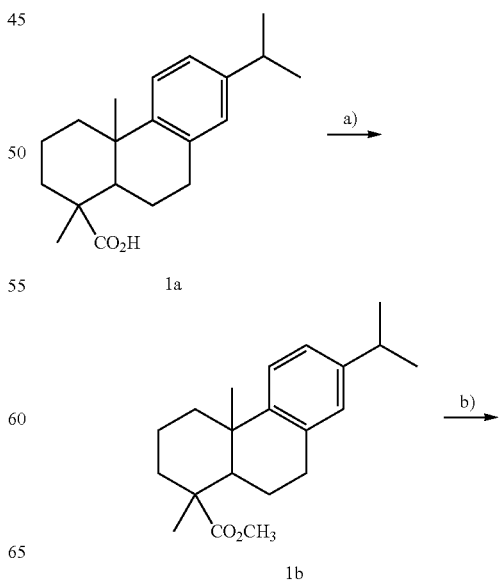

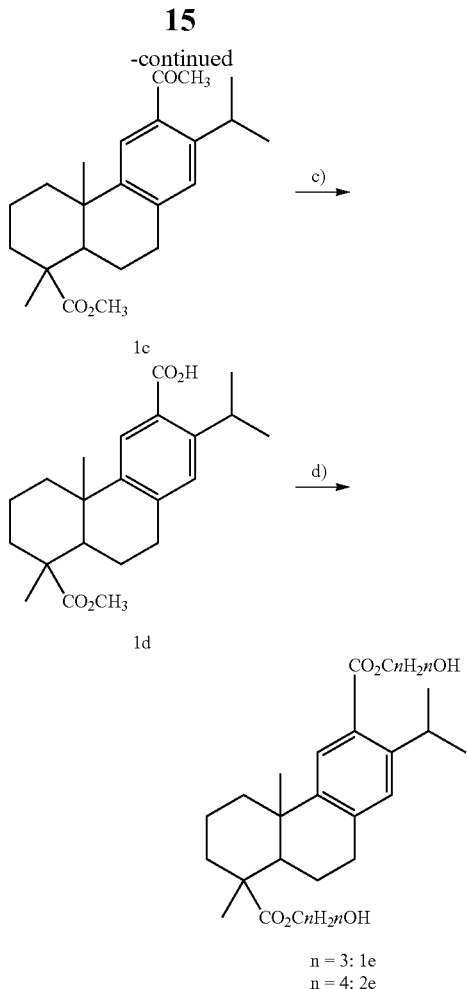

n = 3: 1e
n = 4: 2e

To a mixture of 30.0 g of 92% dehydroabietic acid (1a, manufactured by Arakawa Chemical Industries, Ltd.) and 60 ml of methylene chloride, 13.4 g of chloride oxalyl was dropped at room temperature. After stirring for 3 hours, the solvent was evaporated under reduced pressure, and 16.0 g of methanol was dropped thereto. After stirring for 3 hours at room temperature, the excessive amount of methanol was evaporated under reduced pressure, and thus obtaining 31.4 g of white crystals of a compound (1b).

To a mixture of 31.4 g of the compound (1b), 9.4 g of acetyl chloride, and 80 ml of methylene chloride, 29.3 g of anhydrous aluminium chloride was added in small portions at 3 to 5° C. After stirring for 2 hours at 5 to 8° C., the reaction liquid was poured to 500 g of ice water. 200 ml of ethyl acetate was added, and the organic layer was extracted. The organic layer was washed with a saline solution, and dried with anhydrous magnesium chloride. Thereafter, the solvent was evaporated under reduced pressure, 50 ml of cold methanol was added to the residue, and the precipitated white crystals of the compound (1c) were collected by filtration (yield 32.8 g).

32.0 g of sodium hydroxide was dissolve in 100 ml of water, and 25.6 g of bromine was dropped into the solution at 8 to 10° C. Further, a solution prepared by dissolving 17.8 g of the compound (1c) in 100 ml of dimethoxyethane was dropped at 10 to 12° C. The mixture was stirred at room temperature for 2 hours, the reaction liquid was poured to 6N cold dilute hydrochloric acid to make the acidic liquid, and the precipitated white crystals were collected by filtration. The crystals were recrystallized from methanol, and thus obtaining 14.9 g of the crystals of the compound (1d).

The $^1$H-NMR data of the compound (1d) is shown below.

$^1$H NMR (300 MHz, CDCl$_3$) δ 1.20-1.88 (m, 19H), 2.17-2.40 (dd, 2H), 2.91 (t, 2H), 3.66 (s, 3H), 3.87 (m, 1H), 7.07 (s, 1H), 7.86 (s, 1H)

17.9 g of the compound (1d), 38.0 g of 1,3 propanediol, and 228 mg of tetraethyl orthotitanate were placed in a 100-ml three-necked flask equipped with a nitrogen inlet tube, nitrogen was gently blown into the flask, and the flask was heated at 180° C. for 3 hours while methanol generated therein was evaporated. Subsequently, the mixture was allowed to react for 7 hours at 230° C. Under reduced pressure, the excessive amount of 1,3-propanediol was evaporated at 120° C., and thus obtaining 23.0 g of a transparent oily material of the compound (1e).

The $^1$H-NMR data of the compound (1e) is shown below.

$^1$H NMR (300 MHz, CDCl$_3$) δ 1.18-2.05 (m, 23H), 2.17-2.35 (dd 2H), 2.88 (t, 2H), 3.66 (m, 1H), 3.67 (t, 2H), 3.76 (t, 2H), 4.24 (m, 2H), 4.44 (t, 2H), 7.04 (s, 1H), 7.63 (s, 1H)

17.9 g of the compound (1d), 45.0 g of 1,4-butanediol, and 228 mg of tetraethyl orthotitanate were placed in a 100-ml three-necked flask equipped with a nitrogen inlet tube, nitrogen was gently blown into the flask, and the flask was heated at 180° C. for 3 hours while generated methanol was evaporated. Subsequently, the mixture was allowed to react for 8 hours at 230° C. Under reduced pressure, the excessive amount of 1,4-butanediol was evaporated at 130° C., and thus obtaining 24.3 g of a transparent oily material of the compound (2e).

The $^1$H-NMR data of the compound (2e) is shown below.

$^1$H NMR (300 MHz, CDCl$_3$) δ 1.18-1.90 (m, 27H), 2.16-2.35 (dd 2H), 2.87 (t, 2H), 3.65 (m, 1H), 3.67 (t, 2H), 3.69 (t, 2H), 4.08 (m, 2H), 4.30 (t, 2H), 7.01 (s, 1H), 7.62 (s, 1H)

Other 12-carboxydehydroabietic acid derivatives (the following formula) were synthesized in accordance with the above-described method. The compound in which both of X and Y are Cl was obtained by hydrolyzing the compound (1d) with sodium hydroxide, and then allowing the product to react with oxalyl chloride in 1,2-dichloroethane. Their NMR spectrum data ($^1$HNMR (300 MHz, δ)) were shown in Table 1.

TABLE 1

| X | Y | Ha | Hb | Hc | Hd |
|---|---|---|---|---|---|
| OH | OH | 7.57 (s) | 7.05 (s) | 3.68 (m) | 2.87 (dd) |
| OMe | OMe | 7.66 (s) | 7.04 (s) | 3.67 (m) | 2.88 (dd) |
| OPh | OPh | 7.93 (s) | 7.14 (s) | 3.82 (m) | 3.02 (dd) |
| Cl | Cl | 7.99 (s) | 7.09 (s) | 3.56 (m) | 2.98 (dd) |

Example 1

Synthesis of Dehydroabietic Acid Polymer (1)

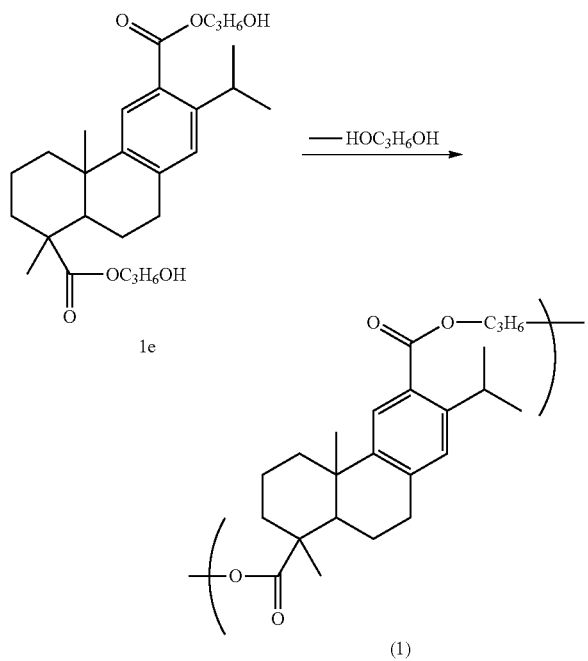

10.0 g of the compound (1e) and 50 mg of tetraethyl orthotitanate were placed in a 50-ml three-necked flask equipped with a nitrogen inlet tube, stirred while nitrogen was gently blown into the flask, the temperature was elevated to 230° C., and the mixture was heated for 3 hours at 230° C. Subsequently, the mixture was allowed to react at 270° C. for 3 hours, under reduced pressure (133 Pa). After cooling, the reactant was dissolved in 50 ml of tetrahydrofuran, and insoluble matter was removed. Thereafter, the solution was poured into 1000 ml of methanol, and the precipitate was collected by filtration. The precipitate was washed with methanol, and dried to obtain 8.2 g of white powder, and used as the dehydroabietic acid polymer (1).

The weight average molecular weight of the dehydroabietic acid polymer (1) was 98,000 as measured by GPC. As a thermophysical property of the dehydroabietic acid polymer (1), the glass transition temperature Tg was 96° C. as measured by DSC at a temperature rising rate of 10° C./minute.

Example 2

Synthesis of Dehydroabietic Acid Polymer (2)

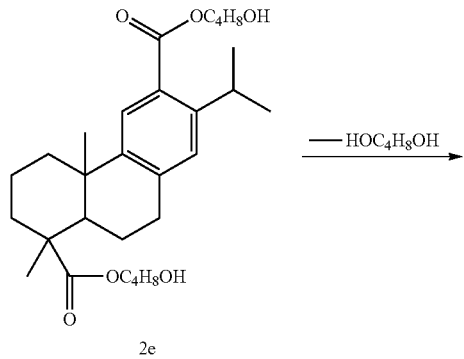

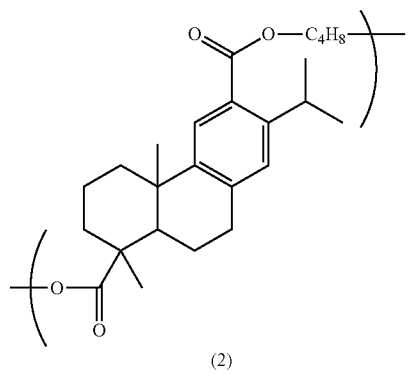

10.5 g of the compound (2e) and 50 mg of tetraethyl orthotitanate were placed in a 50-ml three-necked flask equipped with a nitrogen inlet tube, stirred while nitrogen was gently blown into the flask, the temperature was elevated to 230° C., and the mixture was heated for 3 hours at 230° C. Subsequently, the mixture was allowed to react at 270° C. for 3 hours under reduced pressure (Hb). After cooling, the reactant was dissolved in 50 ml of tetrahydrofuran, and insoluble matter was removed. Thereafter, the solution was poured into 1000 ml of methanol, and the precipitate was collected by filtration. The precipitate was washed with methanol, and dried to obtain 8.4 g of white powder, and used as the dehydroabietic acid polymer (2).

The weight average molecular weight of the dehydroabietic acid polymer (1) was 79,000 as measured by GPC. As a thermophysical property of the dehydroabietic acid polymer (1), the glass transition temperature Tg was 92° C. as measured by DSC at a temperature rising rate of 10° C./minute.

Example 3

Synthesis of Dehydroabietic Acid Polymer (3)

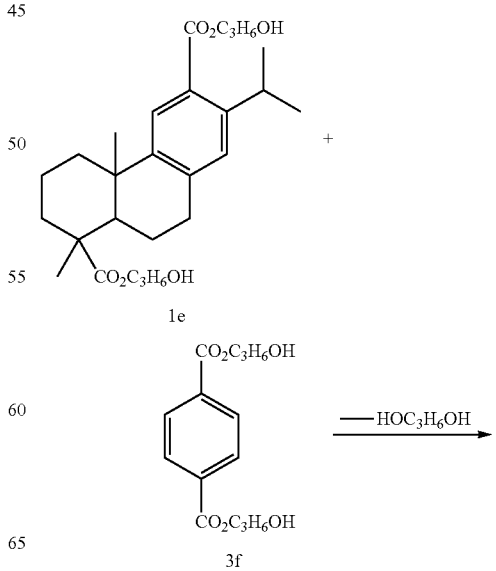

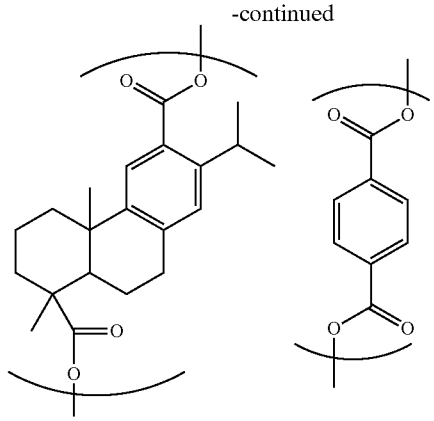

(3)

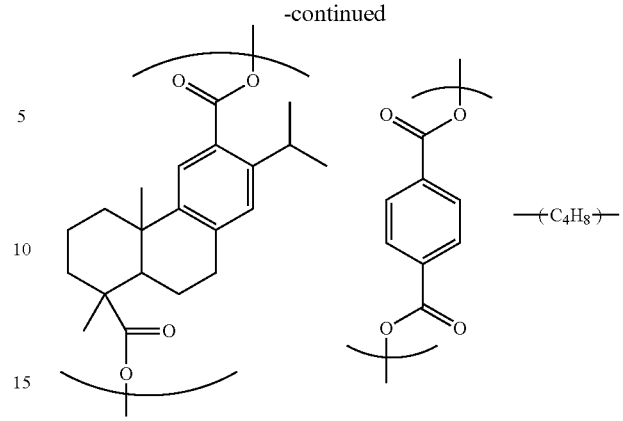

(4)

9.2 g of the compound (1e), 5.65 g of the compound (3f), and 30 mg of antimony oxide were placed in a 50-ml three-necked flask equipped with a nitrogen inlet tube, and stirred under heating at 180° C. for 3 hours while nitrogen was gently blown into the flask. Subsequently, the mixture was heated at 230° C. for 2 hours, and then 270° C. for 2 hours, under reduced pressure. After cooling, 100 ml of tetrahydrofuran was added to the reactant and the reactant was dissolved under heating, and insoluble matter was removed by filtration. Thereafter, the solution was poured into 1000 ml of methanol, and the precipitate was collected by filtration. The precipitate was washed with methanol, and dried to obtain 11.6 g of white powder, and used as the dehydroabietic acid polymer (3).

The weight average molecular weight of the dehydroabietic acid polymer (3) was 128,000 as measured by GPC. As a thermophysical property of the dehydroabietic acid polymer (1), the glass transition temperature Tg was 89° C. as measured by DSC at a temperature rising rate of 10° C./minute.

Example 4

Synthesis of Dehydroabietic Acid Polymer (4)

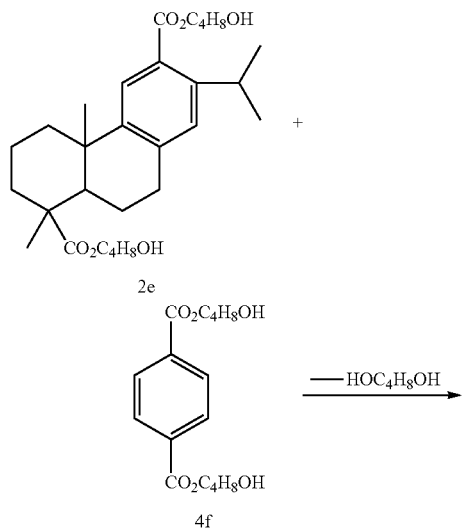

9.8 g of the compound (2e), 6.21 g of the compound (4f), and 30 mg of antimony oxide were placed in a 50-ml three-necked flask equipped with a nitrogen inlet tube, and stirred under heating at 180° C. for 3 hours while nitrogen was gently blown into the flask. Subsequently, the mixture was heated at 230° C. for 2 hours, and then 270° C. for 3 hours, under reduced pressure. After cooling, 100 ml of tetrahydrofuran was added to the reactant and the reactant was dissolved under heating, and insoluble matter was removed by filtration. Thereafter, the solution was poured into 1000 ml of methanol, and the precipitate was collected by filtration. The precipitate was washed with methanol, and dried to obtain 12.0 g of white powder, and used as the dehydroabietic acid polymer (4).

The weight average molecular weight of the dehydroabietic acid polymer (4) was 76,000 as measured by GPC. As a thermophysical property of the dehydroabietic acid polymer (1), the glass transition temperature Tg was 89° C. as measured by DSC at a temperature rising rate of 10° C./minute.

Example 5

Synthesis of Dehydroabietic Acid Polymer (5)

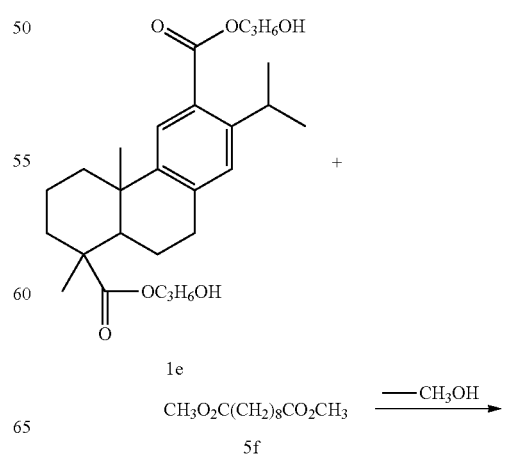

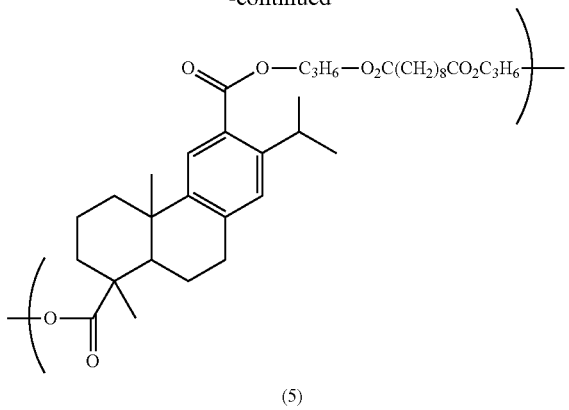

(5)

14.8 g of the compound (1e), 7.4 g of dimethyl sebacate (compound 5f), and 200 mg of antimony oxide were placed in a 50-ml three-necked flask equipped with a nitrogen inlet tube, and stirred under heating at 160° C. for 3 hours while nitrogen was gently blown into the flask. Subsequently, the mixture was heated at 180° C. for 2 hours, and then 260° C. for 2 hours, under reduced pressure. After cooling, 50 ml of tetrahydrofuran was added to the reactant and the reactant was dissolved under heating, and insoluble matter was removed by filtration. Thereafter, the solution was poured into 1000 ml of methanol, and the precipitate was collected by filtration. The precipitate was washed with methanol, and dried to obtain 16.3 g of ash gray resinoid, and used as the dehydroabietic acid polymer (5).

The weight average molecular weight of the dehydroabietic acid polymer (5) was 61,000 as measured by GPC. As a thermophysical property of the dehydroabietic acid polymer (1), the glass transition temperature Tg was 37° C. as measured by DSC at a temperature rising rate of 10° C./minute.

[Evaluation]

The dehydroabietic acid polymers (1) to (5) obtained in Examples 1 to 5 and a commercial PLA (polylactic acid) as the comparative polymer in Comparative Examples 1 to 3 were subjected to the comparative evaluations of physical properties including notched Charpy impact strength as the index of impact resistance, water absorption rate (%) as the index of resistance against moisture and water, and film toughness. The results are shown in Table 2.

The following polymer was used in comparative examples.

Comparative Example 1

PLA: Polylactic Acid Manufactured by Mitsui Chemicals, Inc., product name: LACEA H-140, Tg: 58° C.

<Charpy Impact Test>

The notched charpy impact strength was measured in accordance with ISO179, and expressed in terms of $KJ/m^2$.

<Water absorption Rate (%)>

Water absorption rate was measured as follows.

The cast films for the evaluation of film forming ability made using the dehydroabietic acid polymers (1) to (5) in Examples 1 to 5 and the PLA in Comparative Example 1 were impregnated with water at 23° C. for 24 hours. Subsequently, water droplets were wiped from the surface, and the weight was quickly measured. The water absorption rate was calculated by the following formula:

Water absorption rate=(film weight after water impregnation−film weight before water impregnation)/film weight before water impregnation <Film Toughness>

Films having a thickness of 100μ was made by a casting method using 10% methylene chloride solutions of the respective polymers. The toughness or brittleness of the dry films was evaluated by repeated flexibility test (UL746E, n=5). Those achieved an average of 500 times or more were rated as A, from 50 to 500 times as B, and 50 times or less as C.

TABLE 2

| Polymer | Charpy impact test ($KJ/m^2$) | Water absorption rate (%) | Film toughness |
|---|---|---|---|
| Polymer of the invention (1) | 2.3 | 0.19 | A |
| Polymer of the invention (2) | 2.8 | 0.18 | A |
| Polymer of the invention (3) | 4.9 | 0.22 | A |
| Polymer of the invention (4) | 6.3 | 0.2 | A |
| Polymer of the invention (5) | 8.9 | 0.18 | A |
| PLA | 1.6 | 0.62 | B |

As indicated in Table 2, dehydroabietic acid polymers (1) to (5) of the invention obtained in Examples 1 to 5 showed higher resistance against impacts, moisture, and water in comparison with PLA. In addition, they showed high toughness in the form of a film.

The entire contents of Japanese Patent Application No. 2010-25989 filed on Feb. 8, 2010 are incorporated herein by reference.

The invention claimed is:

1. A dehydroabietic acid polymer, comprising a skeleton of formula (A) as a repeating unit:

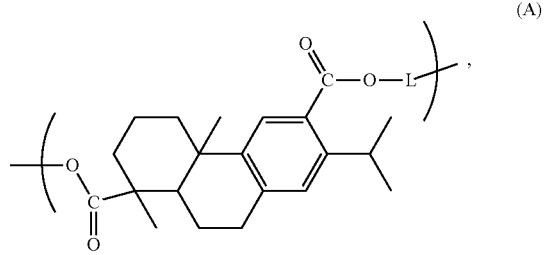

wherein L is selected from the group consisting of: —$(CH_2)_3$—, —$(CH_2)_4$—, —$(CH_2)_{10}$—, —$CH_2CH_2OCH_2CH_2$—, —$CH_2CH_2(OCH_2CH_2)_2$—, —$C_6H_4C(CH_3)_2C_6H_4$—, —$CH_2CH_2OC_6H_4OCH_2CH_2$—, —$CH_2CH_2OCO$-1,4-$C_6H_4COOCH_2CH_2$—, —$CH_2CH_2OCO$-1,3-$C_6H_4COOCH_2CH_2$—, —$C_3H_6OCO$-1,4-$C_6H_4COOC_3H_6$—, —$C_4H_8OCO$-1,4-$C_6H_4COOC_4H_8$— and any combination thereof.

2. The dehydroabietic acid polymer of claim 1, wherein a weight average molecular weight of the polymer is from 5,000 to 500,000.

3. The dehydroabietic acid polymer of claim 1, wherein the polymer is a homopolymer comprising the skeleton of formula (A).

4. The dehydroabietic acid polymer of claim 1, wherein the polymer is a copolymer.

5. A composite material comprising the dehydroabietic acid polymer of claim 1, and a different polymer selected from the group consisting of: polylactic acid, poly-β-hydroxybutyric acid, and polybutylene succinate.

6. The dehydroabietic acid polymer of claim 1, wherein L is selected from the group consisting of: —CH$_2$CH$_2$OCH$_2$CH$_2$—, —CH$_2$CH$_2$(OCH$_2$CH$_2$)$_2$—, —CH$_2$CH$_2$OC$_6$H$_4$OCH$_2$CH$_2$—, —CH$_2$CH$_2$OCO-1,4-C$_6$H$_4$COOCH$_2$CH$_2$—, —CH$_2$CH$_2$OCO-1,3-C$_6$H$_4$COOCH$_2$CH$_2$—, —C$_3$H$_6$OCO-1,4-C$_6$H$_4$COOC$_3$H$_6$—, —C$_4$H$_8$OCO-1,4-C6H4COOC$_4$H$_8$— and any combination thereof.

7. The dehydroabietic acid polymer of claim 1, wherein the skeleton of formula (A) is selected from the group consisting of:

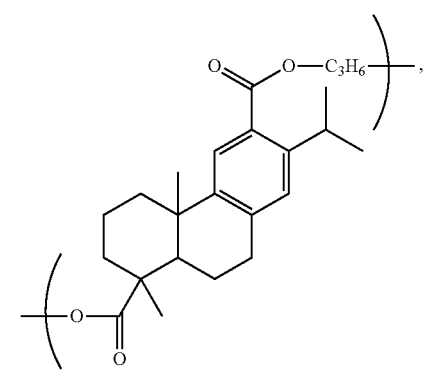
(1)

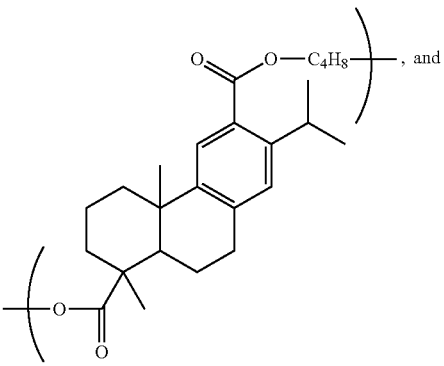
(2) and

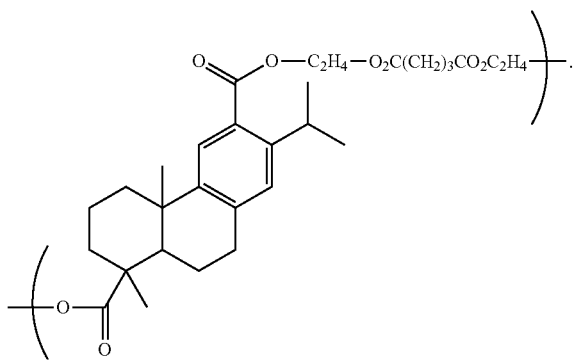
(5)

8. The dehydroabietic acid polymer of claim 4, wherein the another monomer unit is one or more selected from the group consisting of:

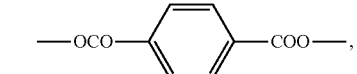

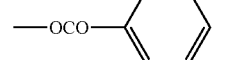

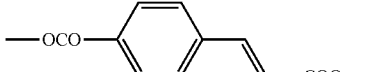

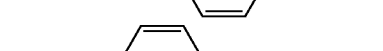
and

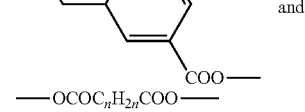

wherein n is an integer from 2 to 10.

9. The dehydroabietic acid polymer of claim 4, wherein the molar ratio between the repeating unit represented by formula (A) and the another monomer unit is 1:0.5 to 1:2.

\* \* \* \* \*